United States Patent [19]

Grenouillet

[11] Patent Number: 5,176,149
[45] Date of Patent: Jan. 5, 1993

[54] CATHETER GUIDE SUPPORT

[75] Inventor: Guy Grenouillet, Villers-Le-Lac, France

[73] Assignee: Nivarox-FAR S.A., Le Locle, Switzerland

[21] Appl. No.: 814,331

[22] Filed: Dec. 27, 1991

[30] Foreign Application Priority Data

Dec. 28, 1990 [FR] France .................. 90 16579

[51] Int. Cl.⁵ .......................................... A61M 25/01
[52] U.S. Cl. .................... 128/772; 128/657; 604/164; 604/170; 604/280; 604/282
[58] Field of Search ............... 128/772, 657; 604/164, 604/170, 280, 282; 606/194, 192

[56] References Cited

U.S. PATENT DOCUMENTS

| 3,528,406 | 9/1970 | Jeckel et al. | |
|---|---|---|---|
| 3,789,841 | 2/1974 | Antoshkiw | 128/772 |
| 4,721,117 | 1/1988 | Mar et al. | |
| 4,724,846 | 2/1988 | Evans, III | 128/772 |
| 4,884,579 | 12/1989 | Engelson | 604/170 |

FOREIGN PATENT DOCUMENTS

| 0132694 | 8/1984 | European Pat. Off. |
|---|---|---|
| 0255234 | 6/1987 | European Pat. Off. |
| 8707493 | 12/1987 | European Pat. Off. |
| 8910088 | 11/1989 | World Int. Prop. O. |
| 9001892 | 3/1990 | World Int. Prop. O. |

Primary Examiner—Lee S. Cohen
Assistant Examiner—Brian L. Casler
Attorney, Agent, or Firm—Weil, Gotshal & Manges

[57] ABSTRACT

A catheter guide support is provided having a wire with a proximal region, of substantially constant cross-section, a distal tapered region and a flexible protecting sheath which extends at least along the length of the distal region of the wire. The wire is constructed integral with the sheath only at the free extremity of its distal region by means of a first weld forming a rounded end, said support also having a tube extending over the whole region of the wire not covered by the sheath, one extremity of the tube simply abutting against the proximal region of the sheath whereas the opposite extremity of the tube is fixed to the proximal region of the wire by means of a second weld.

12 Claims, 1 Drawing Sheet

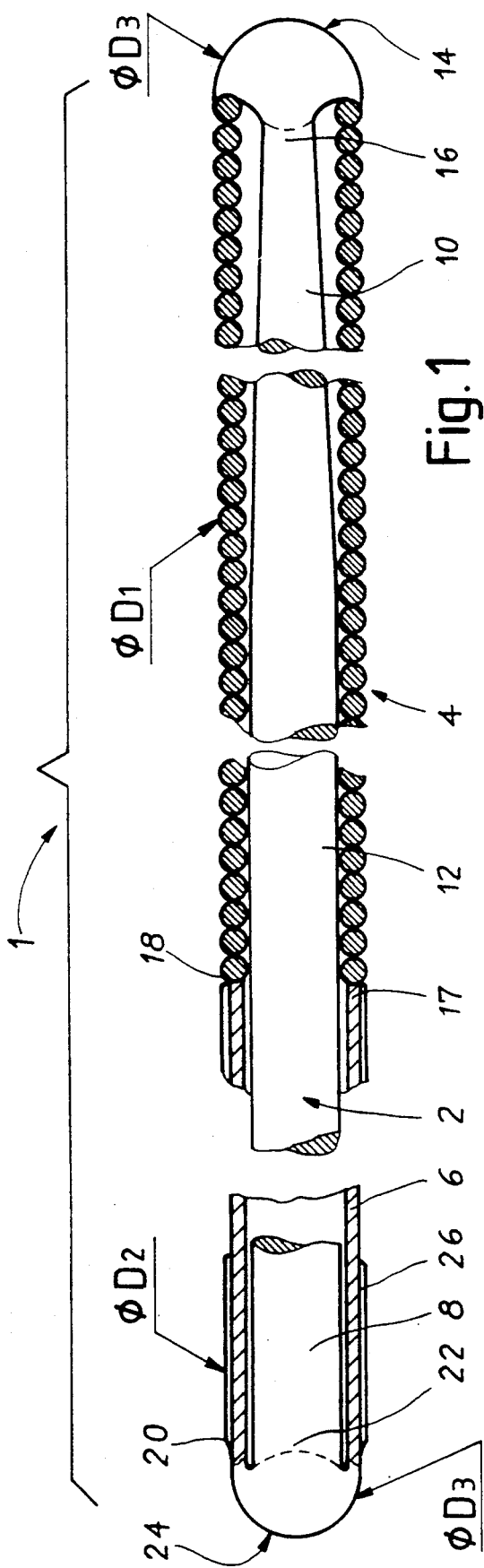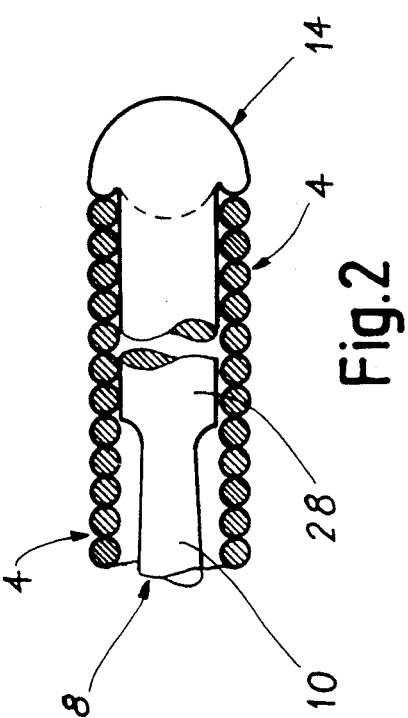

CATHETER GUIDE SUPPORT

FIELD OF THE INVENTION

The instant invention relates to guide supports in general and in particular to guide supports adapted to be introduced and guided in blood vessels of small diameter in order to facilitate the introduction of a catheter into the latter.

This type of guide support for catheters is useful for many applications notably in the field of cardiovascular surgery such as, for example, in cardiovascular angioplasty, during which a catheter is introduced into a constricted region in the coronary artery of a patient and the catheter is then inflated in order to dilate the passage of the artery.

DESCRIPTION OF THE PRIOR ART

It is already known from the specification of U.S. Pat. No. 4,545,390 to provide a guide wire for a catheter, the latter having a small diameter ($\leq 0.5$ mm) and being adapted to be introduced by the endovenous route into the human body.

According to this specification, the guide support has a stainless steel wire having a tapered zone in its distal region onto which is threaded a helical spring having a diameter substantially equal to the diameter of the main wire. The proximal end of the spring is fixed to the wire by soldering in the region of the wire where the latter begins to taper and the distal extremity of the spring is also soldered to the distal extremity of the wire.

Such a guide support generally works in a satisfactory manner but does, however, have certain disadvantages.

Thus, during the fixing of the spring to the wire by soldering, the latter is heated to temperatures ($\simeq 500°$ C.) which approach the temperatures at the beginning of the crystallographic transformation of stainless steels and which correspond to the annealing of the latter, and at which the mechanical properties of these steels begin to deteriorate very substantially. It will thus be readily understood that this annealing which occurs during the soldering operation, could lead to premature rupture of the wire during use, such rupture being liable to cause serious complications if it were to occur within the vein of a patient.

Furthermore, guide supports such as are described in the above mentioned specification have an extra thickness at the point of the solder which carries the risk of impeding or even blocking the catheter when the latter slides on the support.

In addition, when the wire, which is generally coated with a layer of a material having a low coefficient of o friction, such as TEFLON ®, is associated with a helical spring coated with gold for biocompatability reasons, the soldering of the spring onto the wire causes a deterioration both of the gold layer and also of the layer of material having a low coefficient of friction prejudicial to the biocompatibilty of the guide support.

OBJECTS OF THE INVENTION

It is therefore a principle object of the instant invention to overcome the above mentioned disadvantages of the prior art and to provide a guide support for a catheter having improved operational reliability.

BRIEF SUMMARY OF THE INVENTION

For this purpose, it is an object of the invention to provide a guide support for a catheter having a wire having a proximal region of substantially constant section and a tapered distal region and a flexible protective sheath extending at least over the length of the distal region of the wire.

In accordance with the invention, the wire is attached to the sheath only at the free end of its distal region by means of a first weld forming a rounded tip and the support also having a tube extending over the whole of that part of the wire not covered by the sheath, one end of the tube simply abutting against the proximal region of the sheath whereas the opposite end of the tube is fixed to the proximal part of the wire by a second weld.

Due to these characteristics, the weld of the protective sheath on the operating part of the wire is eliminated. Thus, the mechanical properties of the wire in the areas where it is subjected to mechanical stress, especially by bending, when the support is employed in the body of a patient are not in danger of being changed, for example by annealing of the material at the point of the weld when the sheath is welded to the wire, so that the operational reliability of the support is increased.

According to a preferred embodiment of the invention, the wire also comprises, at the free end of its distal region a reinforcing section having a cross-section substantially equal to the proximal region of the wire.

Such a reinforcing section makes the end of the support more rigid and facilitates the introduction of the latter into the veins of the patient especially in their more sinuous passages.

BRIEF DESCRIPTION OF THE DRAWINGS

Further characteristics and advantages of the invention will appear from a reading of the specification which explains the various embodiments of the invention, which are given by way of non-limiting illustration only and in connection with the accompanying drawings in which:

FIG. 1 is a fragmented section of one embodiment of the guide support according to the invention; and FIG. 2 is a sectional view of the distal part of another embodiment of the guide support according to the invention.

DETAILED DESCRIPTION OF THE INVENTION

Referring to FIG. 1, it will be seen that there is a guide support for a catheter according to the invention designated by the general reference numeral 1. Such a guide support is readily used in medicine for carrying out angioplasty techniques, especially for facilitating the introduction and positioning of a catheter for exploratory, treatment or similar purposes in the cardiovascular system of a patient. In order to position a catheter, it is thus necessary as a first step to introduce the guide support up to the point where treatment of the cardiovascular system is needed and then, in a second step, to slide the catheter required on the support up to the zone to be treated.

As is clearly shown in FIG. 1, the guide support for the catheter comprises a wire 2 forming the bore of the support on which is threaded and made integral with the wire, the protective sheath 4 and a tube 6.

The wire 2, which is preferably made of stainless steel for biocompatability reasons, has a proximal region 8 of constant cross section and a tapered distal section 10.

The proximal region 8 is of generally cylindrical form and the distal region 10 is of generally truncated form.

Typically, the diameter of the region 8 of the part of the wire of constant cross-section is of the order of 0.5 mm and the diameter of the end of the distal region of the wire is of the order of 0.1 mm.

The protective sheath 4 is formed by a helical spring with contiguous spirals. This sheath extends over the distal part 10 of the wire and slightly further over a cylindrical portion 12 of the wire on which it rests. In this connection it should be noted that the internal diameter of the sheath is substantially adjusted to the diameter of the proximal part of the wire.

In accordance with the invention, the sheath 4 is fixed to the wire 2 by a single weld 14 at the free end 16 of the distal region 10 of the wire.

The weld 14 is advantageously a rounded end of the type which will minimise risk of injury to the internal walls of the cardiovascular system during introduction of the support.

The tube 6, threaded over the entire proximal region 8 of the wire which is not covered by the sheath 4, abuts simply at its end 17 against the proximal region 18 of the sheath 4 and is fixed at its end 20 opposite the end 22 of the proximal part 8 of the wire by means of a weld 24 which also has a rounded tip.

Preferably, and as is shown in FIG. 1, the outside diameter D1 of the sheath 4 and that of the tube D2 are substantially equal. In a typical situation, the diameter of these two elements is less than or equal to 0.8 mm according to the specific applications of the support.

Furthermore, it will be noted that the diameter D3 of the rounded tips is also substantially equal to that of the tube 6 and to that of the sheath 4. In this way, by means of the rounded shape and the dimension of the end, the risk of lesions to the internal walls of the veins during introduction of the support is greatly diminished and the introduction of the support is greatly facilitated.

It will also be seen that in the embodiment of the support shown, the tube 6 is coated over its entire length with a layer 26 of a material having a low coefficient of friction such as TEFLON ®. This layer 26 facilitates on the one hand the introduction of the support into the cardiovascular system of the patient and on the other hand and more importantly the sliding of the catheter on the support when the latter is inserted into the body of the patient.

It will thus be readily understood, that with the support structure of the invention, the tube 6 may as a first step be covered with the layer 26 without the former being subject to wear in the active zones of the support at the moment when the tube or the sheath is welded, according to the invention, all welding of the active region of the wire has been eliminated in order to transfer them into neutral zones, that is to say in non-operational zones.

In the embodiment shown, the sheath 4 is made from a biocompatible metal which preferably has radiolabile properties so that the extremity of the support may be rendered visible by fluoroscopy and thus permit guiding and precise positioning of the support in the cardiovascular system. By way of example, an alloy of platinum and iridium, containing 70 to 80% of platinum and 30 to 20% of iridium was used for the manufacture of the sheath 4.

It is of course quite clear that in the situation where the radiolabile alloy forming the sheath is not biocompatible, as is for example the case with tungsten, one may cover the sheath with a metal coating that is biocompatible, such as gold. Here, too, it will be noted that the absence of any weld in the active area of the support prevents deterioration of the coating layer rendering the metal biocompatible.

In the embodiment which has been described, the total length of the support is of the order of 200 mm. Clearly, this length may vary according to the use in question and more precisely as a function of the distance separating the place on the body where the support is introduced from the zone in the cardiovascular system which is to be treated.

As far as the length of the tapered distal part of the wire on which the sheath is threaded, is concerned, it is preferably substantially less than or equal to 80 mm and this length may vary as a function of the rigidity required in the distal part of the wire.

Referring now to FIG. 2, in which the same features are identical to those described in connection with FIG. 1 are identified using the same reference numerals, a variation of an embodiment of a support according to the invention is shown.

According to this variation, the distal region 10 of the wire 2 comprises, at its end part, a reinforcing section 28 having a section substantially equal to the proximal section of the wire 2.

In this embodiment of the invention, the length of the reinforcing section 28 is of the order of 10 mm. A reinforcing section of this type enables the end region of the sheath to be supported and prevents any substantial deformation of this zone of the sheath that is subjected to substantial stress during introduction of the support so that its introduction into the veins is facilitated. It will be further understood that the length of this reinforcement cannot exceed a limited length since otherwise the flexibility of the end region of the support would be reduced and would impede precise guidance of the support in the cardiovascular system and especially in the case where the end of the support has to follow a very sinuous path.

The structure of the support according to the invention enables the elimination of any welding of the active part of the wire 2 with the result that the risk of annealing of the material forming the wire is eliminated. It is also a fact that by dispensing with one of the welds, the manufacturing process is rendered more rapid and economical, the two welds 14 and 24 are welds which are preferably carried out using a microplasma process without the addition of any metal. In this case, it may be noted in an advantageous manner that the material of the two elements to be connected are fused together in an manner such that there is no annealing of the materials.

It may also be noted that, due to the construction of the support, there is a reduction in the length of the tapered part, since it is not necessary to have a section of the tapered part for the welding of the sheath onto the wire. This makes this part easier to manufacture by milling.

I claim:

1. A catheter guide support comprising a wire having a proximal region of substantially constant cross-section and a tapered distal region, and a flexible protecting sheath extending at least along the length of the distal region of the wire, wherein the wire is fixed to the sheath only at the free end of its distal region by means of a first weld forming a rounded tip and which also comprises a tube extending over the whole region of the wire not covered by the sheath, one end of the tube simply abutting against the proximal region of the sheath, whereas the opposite end of the tube is fixed to the proximal region of the wire by means of a second weld.

2. A guide support according to claim 1, wherein the wire also comprises at the extremity of its distal region a reinforcing section having a cross-section substantially equal to that of the proximal region.

3. A guide support according to claim 1, wherein the first and second welds are microplasma welds without added metal.

4. A guide support according to claim 1, wherein the sheath is formed by a helical spring of adjoining spirals.

5. A guide support according to claim 1, wherein the tube and the sheath have substantially the same diameter.

6. A guide support according to claim 5, wherein the tube and the sheath have a diameter substantially equal to or less than 0.8 mm.

7. A guide support according to claim 1, wherein the length of the distal part of the wire is substantially greater than or equal to 80 mm.

8. A guide support according to claim 1, wherein the diameter of the rounded tip portion is substantially equal to the diameter of the tube and the sheath.

9. A guide support according to claim 1, covered by a layer of a material having a low coefficient of friction.

10. A guide support according to claim 1, wherein the tube and the wire are made of stainless steel.

11. A guide support according to claim 1, wherein the sheath is made of a radiolabile material.

12. A guide support according to claim 1, wherein the sheath is made of an alloy of platinum and iridium.

* * * * *